(12) United States Patent
Paul et al.

(10) Patent No.: US 6,241,991 B1
(45) Date of Patent: Jun. 5, 2001

(54) AVIADENOVIRUS

(75) Inventors: Guntram Paul, Bedburg-Hau; Michael Bernhard Hess, Falkensee, both of (DE)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/257,485

(22) Filed: Feb. 25, 1999

(30) Foreign Application Priority Data

Mar. 5, 1998 (EP) .................................................. 98200668

(51) Int. Cl.$^7$ ............................. A61K 39/235; C12N 7/00
(52) U.S. Cl. .................... 424/233.1; 424/816; 435/235.1
(58) Field of Search .............................. 435/235.1, 325.1; 424/225.1, 233.1, 816; 536/23.72

(56) References Cited

FOREIGN PATENT DOCUMENTS

WO 92/00372    9/1992  (WO) .

OTHER PUBLICATIONS

Guy et al, Avian Diseases 41:726–731, 1997.*
Kataria et al, Indian Journal of Comparative Microbiology, Immunology and Infectious Diseases vol. 18 (1): p. 38–42, abstract only cited, 1997.*
Kaur et al, Tropical Animal Health and Production vol. 29 (3) : p. 141–146, abstract only cited, 1997.*
Ziedler et al, Monatshefte fur Veterinarmedizin vol. 39 (16) : p. 56–559, abstract only cited, 1984.*
Raue et al., J. Virol. Methods , vol. 73, pp. 211–217 (Aug. 1998).
Avian Pathology "Growth analysis of adenoviruses isolated from pigeons in chicken cells and serological characterization of the isolates " (1998), Hess et al, vol. 27 (20) p. 196–199.

* cited by examiner

*Primary Examiner*—Mary E. Mosher
(74) *Attorney, Agent, or Firm*—William M. Blackstone

(57) ABSTRACT

The invention relates to a new aviadenovirus which was isolated from a pigeon. The aviadenovirus according to the present invention comprises group-I specific antigen and cannot be neutralized by antiserum against any of the FAV serotypes 1–12. The present invention also relates to an antibody or antiserum immunoreactive with a fibre of the new aviadenovirus, a fibre thereof as well as a vaccin against PiAV related diseases comprising a chemically or physically inactivated virus an attenuated virus, a fibre or fragment thereof, a host cell transformed with a nucleic acid sequence encoding an amino acid sequence comprising an immunogenic determent or a functional variant thereof of a fibre of the aviadenovirus according to the present invention, together with a pharmaceutical carrier.

5 Claims, 1 Drawing Sheet

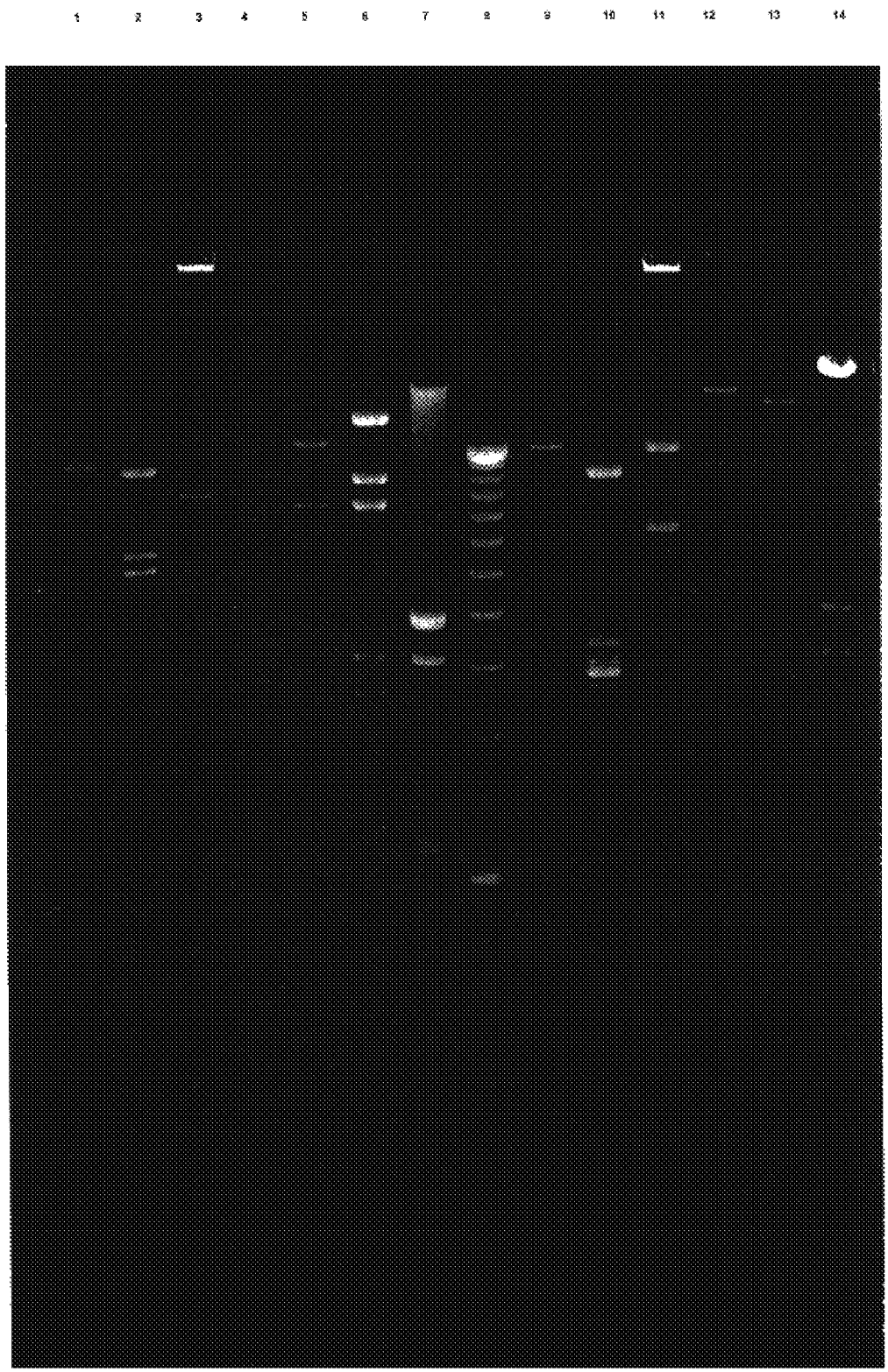
Figure 1/1

AVIADENOVIRUS

FIELD OF THE INVENTION

The present invention relates to a new aviadenovirus.

BACKGROUND OF THE INVENTION

Aviadenoviruses can be subdivided into three groups:

Group I adenoviruses, a subclass of which comprises the fowl adenoviruses (FAV) having a genomic DNA length of ±43.8 kb and two fibres protruding from one pentonbase. The Group I viruses share a common antigen ('group antigen') which distinguishes them from Group II and Group III viruses (ref. 1,9).

Group I adenoviruses can be isolated from different avian species and have been classified as Fowl adenoviruses (FAV), Goose adenoviruses (GAV), Duck adenoviruses (DAV) and Turkey adenoviruses (TAV). The length of the two fibres of FAVs is different for each of the 12 serotypes. In addition to serological typic, the viruses can be characterized by analysis of their DNA. Based on BamHI and HindIII cleavage of the DNA of FAV serotypes 1–11, five subgroups are recognized (ref. 1,4,6,9).

Group II adenoviruses, having Group II specific antigen, comprise a small number of viruses, such as the turkey Haemorrhagic Enteritis virus. These viruses have a genomic DNA length of ±25.5 kb and sport one fibre per penton base.

Group III adenoviruses, of which the Egg Dropping Syndrome causing virus (EDS) is the only serotype, have a genomic DNA length of 33.2 kb and a single fibre per penton base. EDS is serologically not directly related to Group I viruses (ref. 11).

SUMMARY OF THE INVENTION

The aviadenovirus according to the present invention comprises group I-specific antigen and cannot be neutralized by antiserum against any of the FAV serotypes 1–12. Group I specific antigen has not been characterized, but an antiserum obtained using viruses from one of the FAVs is capable of recognizing the other FAVs. This immunoreaction can be detected by using immunofluorescence methods well-known in the art, such as described in ref. 13. In the present invention, and in accordance with ref. 7, the term neutralisation is defined as the ability of an antiserum raised against a particular virus to inhibit virus propagation of another virus.

The new aviadenovirus was isolated from the liver of a pigeon. It is well known that aviadenoviruses can pass species barriers. As yet, the new virus has not been isolated from other avians, which may indicate that it is a primary pigeon adenovirus. Hence, it has been given the name Pigeon AdenoVirus (PiAV).

DETAILED DESCRIPTION OF THE INVENTION

DNA analysis of the PiAV using restriction enzymes BamHI and HindIII result in patterns that do not correspond to any of the five DNA types A–E recognized so far. In fact it did not correspond to the pattern of all known Group I adenoviruses, including GAV and TAV. In addition, it has been found that antiserum against any of the FAV serotypes 1–12 could not neutralise the virus according to the present invention, further proving the unique nature of PiAV.

A sample of the aviadenovirus isolate PiAV 197/5 was deposited on Mar. 3, 1998 with CNCM of the Institute Pasteur (25, Rue du Docteur Roux, F-75724 Paris CEDEX 15, France) under accession number I-1988.

The invention also relates to an antibody or antiserum immunoreactive with a fibre of the aviadenovirus according to the invention.

Preferably, the aviadenovirus according to the invention is a PiAV which in a cross-neutralisation test has a homologous:heterologous titre ratio of 8 or more in both directions with PiAV isolate as deposited under I-1988. More preferably the PiAV according to the invention has a homologous:heterologous titre ratio of 16 or more, in particular of more than 16.

Such an antibody is useful for the immunological detection of PiAV in avians suspected of contracting it.

The invention also relates to a fibre or a synthetic or proteolytically obtained fragment thereof of the aviadenovirus according to the invention.

These fibres or fragments thereof, comprising an antigenic determinant, are useful for generation of monoclonal antibodies, and for the development of a vaccine.

Furthermore the invention relates to a nucleic acid sequence encoding an amino acid sequence, said amino acid sequence comprising an immunogenic determinant or a functional variant thereof of a fibre of the aviadenovirus according to the invention.

Such a nucleic acid sequence is useful for transformation of a host cell or a host virus, which may be used to develop a vaccine.

Accordingly, the present invention relates to a host cell transformed with a nucleic acid sequence according to the invention.

Such a host cell may be used for the preparation of a vaccine, or for the generation of a large amount of amino sequences comprising an immunogenic determinant, said amino sequences being useful for vaccination purposes and obtaining monoclonal and polyclonal antibodies.

Finally, the present invention relates to a vaccine against PiAV related diseases, comprising an attenuated virus, a chemically or physically inactivated virus, a fibre or a fragment thereof, a host cell transformed with the nucleic acid sequence together with a pharmaceutical carrier.

Aviadenoviruses according to the present invention can be obtained by conventional methods. Briefly, a susceptible substrate is inoculated with PiAV and propagated until the virus replicated to a desired titre after which PiAV containing material is harvested.

Every substrate which is able to support the replication of PiAV can be used in the present invention, for example chicken embryo liver cells.

The vaccine according to the invention containing live attenuated virus can be prepared and distributed in the form of a suspension or in a lyophilized form and additionally contains a pharmaceutically acceptable carrier or diluent customary used for such compositions. Carriers include stabilizers, preservatives and buffers. Suitable stabilizers are, for example SPGA, carbohydrates (such as sorbitol, mannitol, starch, sucrose, dextron, glutamate or glucose), proteins (such as dried milk serum, albumin or casein) or degradation products thereof. Suitable buffers are for example alkali metal phosphates. Suitable preservatives are thimerosal, merthiolate and gentamicin. Diluents include water, aqueous buffers (such as buffered saline) and polyols (such as glycerol).

If desired, the live vaccines according to the invention may contain an adjuvant.

The aim of inactivation of PiAV harvested after the propagation step is to eliminate reproduction of the viruses. In general, this can be achieved by chemical or physical means. Chemical inactivation can be effected by treating the viruses with, for example, enzymes, formaldehyde, β-propiolactone, ethyleneimine or a derivative thereof. If necessary, the inactivating compound is neutralized afterwards. Material inactivated with formaldehyde can, for example, be neutralized with thiosulphate or sodium metabisulphite. Physical inactivation can preferably be carried out by subjecting the viruses to energy-rich radiation, such as UV light, X-radiation or γ-radiation. If desired, the pH can be brought back to a value of about 7 after treatment.

Preferably, an inactivated vaccine according to the invention comprises one or more compounds with adjuvant activity. Suitable compounds or compositions for this purpose include aluminium hydroxide, -phosphate or -oxide, oil-in-water or water-in-oil emulsion based on, for example a mineral oil, such as Bayol™ or Marcol 52™ or a vegetable oil such as vitamin E acetate and saponins.

To obtain attenuated PiAV, the virus can be used to infect embryonated eggs and subsequently propagation and passaging of the virus in embryonated eggs by methods known in the art for this purpose.

The vaccine according to the invention comprises an effective dosage of aviadenoviruses according to the present invention as the active component, i.e. an amount of immunizing PiAV material that will induce immunity in the vaccinated birds against challenge by a virulent PiAV. Immunity is defined herein as the induction of a significant higher level of protection in a population of birds after vaccination compared to an unvaccinated group. An effective dosage of PiAV is for example $10^3$–$10^8$ inactivated infectious virus particles. Live vaccines may comprise $10^2$–$10^5$ infectious particles per dose.

Inactivated or live vaccines are administered preferably parenterally, e.g. intramuscularly or subcutaneously.

DETAILED DESCRIPTION OF THE DRAWINGS

The present invention will be described by way of example with reference to the drawing, in which FIG. 1 represents a picture of an agarose gel after electrophoresis, showing DNA patterns obtained after digestion of viral DNA with restriction enzymes.

EXPERIMENTAL SECTION

A) Isolation of the Virus

From a dead pigeon delivered for autopsy in order to determine the cause of death the liver was removed. After homogenization the liver was co-cultivated with primary chicken embryo liver cells (ref. 2). A cytopathic effect was observed, characterized by focal swelling and rounding of cells, which symptoms resemble those of other adenoviruses (ref. 14).

B) Virus Characterization

1. Genomic Differences a) Length

DNA was prepared as described by Bauer et al. (ref. 3) and the virus genome length was determined using the method described by Zsak, I. L. et al (ref. 6) using 1 kb Ladder (Life Technologies) as standard. The length was found to be ±44 kb, which is in the range of group I viruses (ref. 5, 15).

b) Restriction enzyme-analysis (DNA mapping)

The double-stranded PiAV DNA was digested with the restriction enzymes BamHI and HindIII as described by Zsak. L. et al. (ref. 6). Briefly, the adenoviruses were incubated with proteinase K and the released DNA was purified by phenol chloroform extraction. The DNA concentration was measured fluoremetrically at 260 nm. From each DNA 0,3 μg was taken for digestion. Zsak et al. classified the FAV serotypes into five different groups (A–E). As shown in FIG. 1, the pattern (lanes 6 and 14) obtained after digestion with the above restriction enzymes does not correspond to any of the classes A–E, using a prototype virus for each class (lanes 1–5 and lanes 9–13).

TABLE I

Legenda for FIG. 1.

| Lane | Serotype | Strain | DNA-group |
|---|---|---|---|
| 1 and 9 | FAV-1 | CELO | A |
| 2 and 10 | FAV-3 | SR49 | D |
| 3 and 11 | FAV-11 | C2B | C |
| 4 and 12 | FAV-5 | 340 | B |
| 5 and 13 | FAV-7 | YR36 | E |
| 6 and 14 | PiAV | 197/5 | — |

Lanes 1–6 BamHI digestion
Lanes 9–14 HindIII digestion
Lane 7 Molecular weight marker (Boehringer Mannheim) Range 564–21226 bp
Lane 8 Molecular weight marker 1kB-ladder (Life Technologies) Range 75 bp–12216 bp Furthermore, the pattern obtained for PiAV were compared with BamHI and HindIII restriction enzyme pattern of FAV's and other Group I viruses as published in literature (ref. 6, 16, 17). The PiAV pattern did not correspond to any of the published pattern of Group I viruses.

2. Serological Tests

Experiments were performed using polyclonal antisera obtained from rabit and/or chicken.

2a. Presence of Group-I Specific Antigen

Using a microtitre fluorescent antibody test (ref. 12, 13), it was shown (Table II) that PIAV is immunologically reactive with antibodies against Group-I specific antigen, but not with those against Group II and Group III antigen.

TABLE II

Reactivity of different avian adenovirus sera in immunofluorescent assay against PiAV

| virus type | strain | fluorencense |
|---|---|---|
| FAV 1 | OTE | +[1] |
| FAV 2 | SR48 | + |
| FAV 3 | SR49 | + |
| FAV 4 | KR5 | + |
| FAV 5 | 340 | + |
| FAV 6 | CR119 | + |
| FAV 7 | YR36 | + |
| FAV 8/9 | HungVI | + |
| FAV 10 | A2 | + |
| FAV 11 | C2B | + |
| FAV 12 | UF71 | + |
| PiAV | | + |
| GAV-1 | | + |
| EDS | | − |
| HEV | | − |
| Medium | control | − |

[1]+ indicates presence of positive immunofluorescense,
− indicates absence of immunofluorescense.

2b. Serotyping of PIAV

Neutralization and cross-neutralization tests were carried out in microtitre plates as described by Monreal (ref. 2) and McFerran (ref. 14).

In the first neutralization tests PiAV was used together with antisera against all FAV reference strains (ref. 14) and the three described serotypes of goose adenovirus (GAV 1–3), Turkey adenovirus (TAV 1–2) and Duck adenovirus (DAV 2). PiAV was not neutralized by any of the reference sera used (results for FAV are shown in Table III). The cross neutralization test was carried out with PiAV and all FAV reference strains and antisera, respectively. Sera containing twenty units of antibodies and $100TCID_{50}$ of each virus were used for classification. The PiAV-antiserum reacted with some of the FAV serotypes (Table III). However, the homologous:heterologous titre ratio was at least 16 or higher in both directions. Homologous titre ratios can be found on the diagonal from top-left to bottom-right in Table III. According to the published rules for adenovirus classiafication of the International Committee on "Taxonomy of Viruses", PiAV is a new serotype of FAV (Ref. 7) or a new group-I adenovirus.

TABLE III

Results of cross-neutralization carried out between FAV reference viruses and PiAV Antiserum, FAV type-specific

| Virus | FAV 1 OTE | FAV 2 FR48 | FAV3 SR49 | FAV4 KR5 | FAV5 340 | FAV6 CR119 | FAV7 YR36 | FAV8/9 HungVI | FAV10 A2 | FAV11 C2B | FAV12 UF71 | PiAV |
|---|---|---|---|---|---|---|---|---|---|---|---|---|
| OTE | 320[1] | —[2] | — | — | — | — | — | — | — | — | — | — |
| SR48 | 20 | 10240 | 80 | — | — | — | — | — | 80 | — | — | — |
| SR49 | — | — | 1280 | — | — | — | — | — | — | — | 20 | — |
| KR5 | — | — | — | 320 | — | — | — | — | — | 640 | — | — |
| 340 | — | — | — | — | 640 | — | — | — | — | — | 20 | 40 |
| CR119 | — | 20 | — | — | — | 640 | — | — | — | — | — | 40 |
| YR36 | — | — | — | — | — | — | 320 | — | — | — | — | 80 |
| HungVI | — | 80 | — | — | 20 | — | — | 640 | — | — | — | 80 |
| A2 | — | — | — | — | — | — | — | — | 10240 | — | — | — |
| C2B | — | — | — | 160 | — | — | — | — | — | 5120 | — | 40 |
| UF71 | — | 40 | — | 40 | — | — | — | — | — | — | 640 | 40 |
| PiAV | — | — | — | — | — | — | — | — | — | — | — | 10240 |

[1] Serum titers expressed as the reciprocal of that serum dilution neutralizing 100 $TCID_{50}$ of the respective virus. Results are the means of three tests
[2] "—" represents a serum titer <20

3. Polymerase Chain Reaction (PCR) Primers (designated H3/H4) located in the conserved regions of FAV hexon genes were used in a recently established PCR. Whereas all FAV serotypes react positive, PiAV was negative. In case of multiple infections of a pigeon with FAV and PiAV, this method allows a clear separation. The fact that oligonucleotides located in these two conserved regions of the hexon gene do not hybridize with PiAV DNA, underlines the genomic differences between FAVs and PiAV (ref. 8).

Based on this finding PiAV can be regarded as a new virus within the Aviadenovirus group.

Other primers, designated as H1/H2, react positive with all avian adenoviruses including PiAV, except with GAV 1–3 and HEV. Amplification products specific for PiAV can be detected by restriction enzyme analysis using HaeIII endonuclease (ref. 8). The resulting fragment pattern allows to identify PiAV and to differentiate from the other avian adenoviruses.

REFERENCES

1. Monreal, G. Adenoviruses and adeno-associated viruses of Poultry. Poultry Science Rev. 4, p. 1–27 (1992).
2. Monreal, G. et al. Bestimmung von Antikörpen gegen avi äre Adenoviren im Mikrotiter-Zellkultursystem. Berl. M ünch. Tierärztl. Wschr., 93, 125–128 (1980).
3. Bauer A. et al. Growth of avian adeno-associated virus in chicken cells transfected with fowl adenovirus serotype 1 DNA. J. Virol. Methods, 29, p. 335–340 (1990).
4. Gelderblom, H., et al. The fibres of fowl adenoviruses. Arch Viral. 72, 289–298 (1982).
5. Chiocca, S. et al., The complete DNA sequence and genomic organization of the avian adenovirus CELO. J. Virol. 70, 2938–2949 (1996).
6. Zsak, L., et al., Grouping of fowl adenoviruses based upon the restriction patterns of DNA generated by BamHI and HindIII. Intervirol. 22, 110–114 (1984).
7. Rusell, W. C. et al. in: "Virus Taxonomy". Classification and Nomenclature of viruses. Sixth report of the International Committee on Taxonomy of Viruses. (Murphy, F. A. et al. (eds.), Springer-Verlag Wien/New York, 128–133 (1995).
8. Raue, R. et al., Hexon based PCR's combined with restriction enzyme analysis for rapid detection and differentiation of fowl adenoviruses and egg drop syndrome virus. (submitted for publication in J. Virol. Methods).
9. McFerran, J. B. (1991) Adenoviruses in: B. W. Calnek, H. J. Barnes, C. W. Beard, W. M. Reid & H. W. Yoder (eds.), Diseases of poultry, 9th edition, pp. 552–563 (Ames, Iowa state University Press).
10. Jucker, M. T. et al. (1996), Characterization of the haemorrhagic enteritis virus genome and the sequence of the putative penton base and core protein genes, J. Gen. Virol. 77, 469–279.
11. Hess, M. et al. (1997), The complete nucleotide sequence of the egg drop syndrome virus—an intermediate between mastadenoviruses and aviadenoviruses. Virology, 238, 145–156.
12. Calnek, B. W. et al. (1982) Serological cross-reactivity of avian Adenovirus serotypes in an enzyme-linked immunosorbent assay, Avia Dis., 26, 897–906.
13. Adair, B. M. et al. (1980) Development of a microtitre fluorescent antibody test for serological detection of adenovirus infection in birds, Avia Pathol. 9, 291–300.
14. McFerran J. B. Adenoviruses in: A laboratory manual for the isolation and identification of avian pathogens. 3rd edition. Purchase H. G. et al. (eds). Kendall/Hunt Publishing Company, Iowa, 77–81 (1989).

What is claimed is:

1. An isolated and purified pigeon adenovirus (PiAV) comprising group I—specific antigen, which is not neutralized by antiserum against any of fowl adenovirus serotypes 1–12, and which is immune reactive in a cross-neutralization teat with a titer ratio of less than 16 in both directions with a PiAV isolate deposited with the CNCM under accession number I-1988.

2. The PiAV according to claim 1, wherein the PiAV has a titer ratio of less than 8 in both directions with the PiAV isolate deposited with the CNCM under accession number I-1988.

3. The PIAV according to claim 1, which is PiAV 197/5 deposited on Mar. 3, 1998 with the CNCM under accession number I-1988.

4. A vaccine against PiAV related diseases, comprising a virus according to claim 1, which has been attenuated, together with a pharmaceutical carrier.

5. A vaccine against PiAV related diseases, comprising a pigeon adenoviru of claim 1, which has been inactivated and a pharmaceutical carrier.

* * * * *

UNITED STATES PATENT AND TRADEMARK OFFICE
CERTIFICATE OF CORRECTION

PATENT NO. : 6,241,991 B1
DATED : June 5, 2001
INVENTOR(S) : Paul et al.

Page 1 of 1

It is certified that error appears in the above-identified patent and that said Letters Patent is hereby corrected as shown below:

<u>Claim 1,</u>
Line 5, replace "teat" with -- test --.

<u>Claim 5,</u>
Line 2, replace "adenoviru" with -- adenovirus --.

Signed and Sealed this

Eighth Day of January, 2002

Attest:

JAMES E. ROGAN
*Attesting Officer*     *Director of the United States Patent and Trademark Office*